United States Patent

Ichiki et al.

[11] Patent Number: 5,867,249
[45] Date of Patent: Feb. 2, 1999

[54] OPHTHALMOLOGICAL ANALYZER

[75] Inventors: Hiroshi Ichiki; Akihiro Sugiyama, both of Tokyo, Japan

[73] Assignee: Kabushiki Kaisha TOPCON, Tokyo, Japan

[21] Appl. No.: 862,815

[22] Filed: May 30, 1997

[30] Foreign Application Priority Data

Jun. 2, 1996 [JP] Japan ..................... 8-161145

[51] Int. Cl.$^6$ ..................... A61B 3/00
[52] U.S. Cl. ..................... 351/211
[58] Field of Search ..................... 351/200, 205, 351/206, 208, 211, 246; 396/18

[56] References Cited

U.S. PATENT DOCUMENTS 5,315,329  5/1994  McAdams .................. 351/206
5,374,967  12/1994  Hideshima et al. .......... 351/208

Primary Examiner—George Manuel
Attorney, Agent, or Firm—Baker & Botts, L.L.P.

[57] ABSTRACT

The present invention relates to an ophthalmological analyzer, and an object of the present invention is to provide an ophthalmological analyzer capable of making information on the shape of an optic nerve conform to the test results of an eyeground or a visual field to be tested by using a look-up table or the like. The ophthalmological analyzer comprises a recording unit for recording at least test data on subjects and information on shapes of optic nerves, a data input unit to be operated by a tester to enter characters and values for coordinates, and a controller which carries out an analytical operation on the basis of the test data on the subject and the information on the shape of an optic nerve, read from the recording unit. The controller is capable of selecting a piece of information to be used among a plurality of pieces of information on the shapes of optic nerves, of changing at least part of information on the shape of an optional optic nerve or of producing information on the shape of a new optic nerve.

9 Claims, 17 Drawing Sheets

LENGTH OF EYE AXIS: 2r

P (2r·cos² θ, 2r·cos θ · sin θ)

d = A·r·sin 2θ          A: MAGNIFICATION OF PLANE IMAGE $\theta = \frac{1}{2} \sin^{-1}(\frac{d}{A \cdot r})$

OPHTHALMOLOGICAL ANALYZER

BACKGROUND OF THE INVENTION

The present invention relates to an ophthalmological analyzer and, more specifically, to an ophthalmological analyzer capable of integrating the results of test of an object of analysis, such as the eyeground or the visual field, by using a look-up table or the like.

Definite knowledge of the shapes of optic nerves has not yet been acquired and it has been desired to formulate the shapes of various optic nerves. There are individual differences in the shape of the optic nerve, and the shape of the optic nerve of each patient must be specified by an appropriate type. For example, it is generally known that there are individual differences in the size of the optic nerve papilla, and the shapes of the optic nerves of some people are different from ordinary shapes. A lesion in the optic nerve of a patient appears apparently at different positions depending on the type of a perimeter, the type of a retinal camera, the angle of view of a retinal camera and the position of the eyeball, i.e., the orientation of the eyeball. Therefore, those errors must be taken into account when the rigorous observation of the variation of the lesion with time is required. If the shape of the optic nerve is expressed by a function, which is a conventional practice, it is difficult to change the shape of a necessary portion of the optic nerve, and hence it is difficult to deal with individual differences and the foregoing errors.

The present invention relates to a laser system employing a semiconductor laser or the like and, more particularly, to a laser system capable of operating at a low power consumption.

There have been laser systems employing a semiconductor laser used in various field.

SUMMARY OF THE INVENTION

According to the present invention, a recording unit records at least test data on the subject and data on the shape of the optic nerve, a tester enters characters and values of coordinates by operating a data input unit, and a controller analyzes test data on the subject, and information on the shape of the optic nerve, read from the recording unit. The controller is capable of selecting a piece of information to be used from information on the shape of a plurality of optic nerves, of changing at least part of information on the shape of an optional optic nerve or of producing information on the shape of a new optic nerve.

DESCRIPTION OF THE PREFERRED EMBODIMENTS

Figure 1:
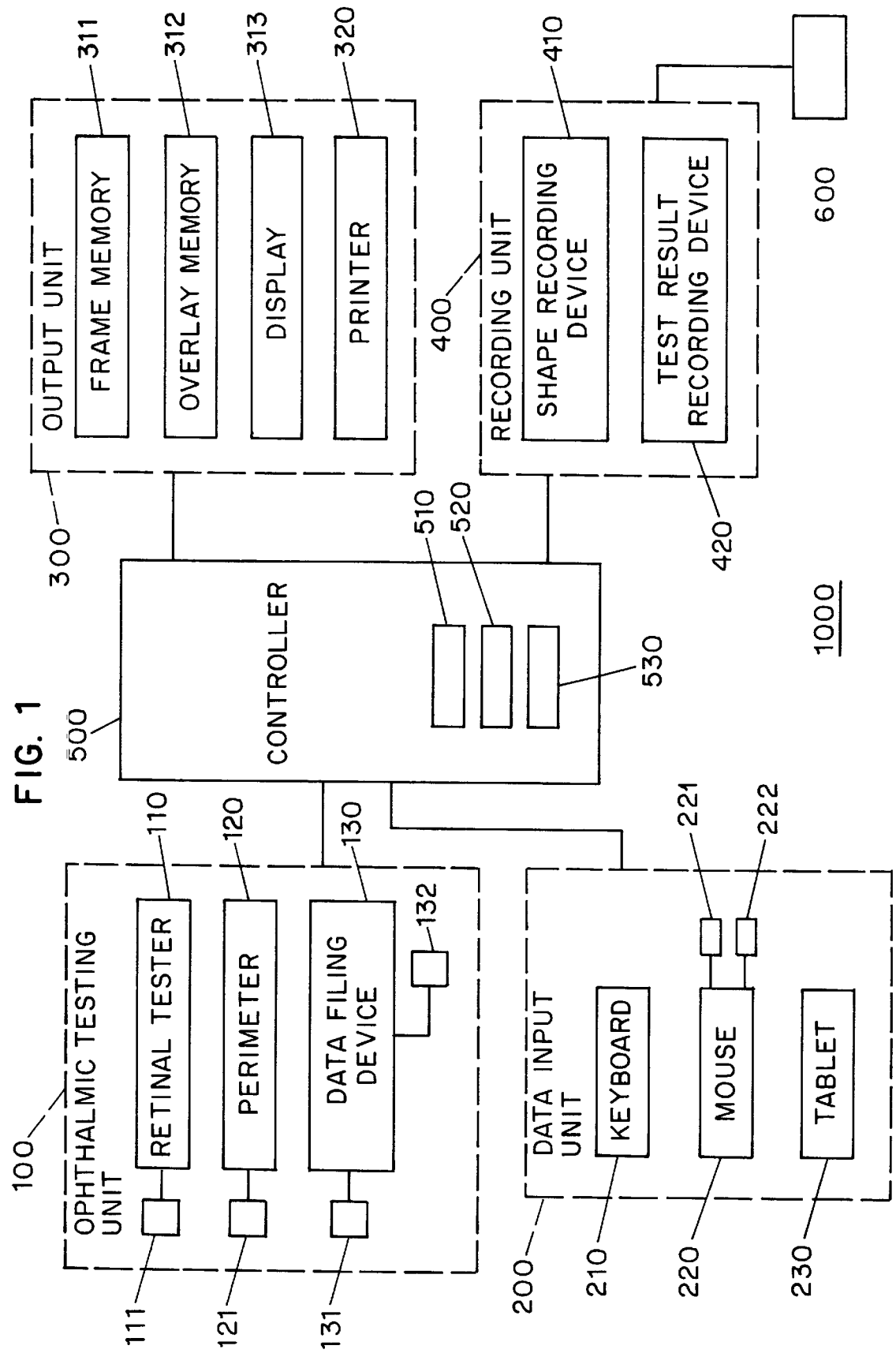
FIG. 1 is a block diagram showing the electrical configuration of an ophthalmological analyzer in a preferred embodiment according to the present invention.

Referring to FIG. 1, an ophthalmological analyzer 1000 in a preferred embodiment according to the present invention comprises an ophthalmic testing unit 100, a data input unit 200 for entering characters and values for coordinates, an output unit 300, a recording unit 400 and a controller 500.

The ophthalmic testing unit 100 is used for ophthamic testing and comprises a retinal tester 110, a perimeter 120, and a data filing device 130. The retinal tester 110 is used, similarly to a retinal camera, SLO and Heiderberg retinal tomography, for producing a picture of the subject's eyeground for observation on the basis of test results. The retinal tester 110 may be provided with a retinal image recorder for recording the image of the eyeground. An eyeground image taking switch 111 is connected to the retinal tester 110. The eyeground image taking switch 111 is operated to send an image taken by the retinal tester 110 to the controller 500, or to send an image stored in a retinal image storage device and reproduced from the retinal image storage device to the controller 500. The perimeter 120, similarly to a static perimeter, a dynamic perimeter and a retinal perimeter, is used for measuring the subject's visual field. The perimeter may be provided with a visual field data storage device for storing visual field data. A visual field taking switch 121 is connected to the perimeter 120. The visual field taking switch 121 is operated to send visual field data obtained by the perimeter 120 to the controller 500 or to send visual field data stored in a visual field data recording device to the controller 500. The data filing device 130 records patient information on the subject including test data obtained by the retinal tester 110, the perimeter 120 and an intraocular pressure tester or the like. A transfer switch 131 and a storage device 132 for storing the patient information are connected to the data filing device 130. The transfer switch 131 is operated to send the patient information stored in the storage device 132 to the controller 500.

The data input unit 200 is operated to enter characters, coordinates and such into the controller 500. In this embodiment, the data input unit 200 is provided with a keyboard 210, a mouse 220 and a tablet 230. The keyboard 210 is operated to give instructions to the ophthalmological analyzer 1000, to enter the patient information into the ophthalmological analyzer 1000, and to provide coordinate data and such for producing and editing information on the shape of the optic nerve.

The mouse 220 moves a cursor displayed on a screen of a display. The position of the mouse 220 and the operation of a right button 221 and a left button 222 are used in combination to give instructions to the ophthalmological analyzer 1000, to enter the patient information into the ophthalmological analyzer 1000, and to provide coordinate data and such for producing and editing information on the shape of the optic nerve. The tablet 230 is used for entering coordinate data by scanning printed matters and handwritten matters. Coordinate data and such can be entered when producing and editing information on the shape of the optic nerve by operating a coordinate data input button 231.

The output unit 300 provides information on the progress and the interim results of analytical operation of the controller 500. The output unit 300 is provided with a frame memory 311, an overlay memory 312, a display 313 and a printer 320. The frame memory 311 stores an image of the eyeground and data on visual field provided by the ophthalmic testing unit 100. The overlay memory 312 stores numeric data on the cursor, characters and such specified or provided by the data input unit 200, data on the shape of the optic nerve, and the progress and the interim results of analytic operations. The display 313 displays the respective contents of the frame memory 311 and the overlay memory 312, and data obtained by combining the respective contents of the frame memory 311 and the overlay memory 312. The printer 320 prints out the data displayed on the screen of the display 313.

The recording unit 400 is provided with a shape recording device 410 and a test result recording device 420. The shape recording device 410 records data representing the shape of the optic nerve, and the test result recording device 420 records the progress and the interim results of analytic operations of the controller 500, and information on the subject's characteristics. The controller 500 analyzes the results of test, such as an image of the eyeground, data on visual field, eye pressure and such, inputted from the ophthalmological analyzer 100.

The controller 500 is provided with a selecting device 510 and an editing device 520. The selecting device 510 selects and reproduces information on the shape of a desired optic nerve among information on the shapes of a plurality of optic nerves stored previously in the recording unit 400 for analysis and diagnosis. The editing device 520 changes the information on the shape of an optic nerve or produces new information on the shape of an optic nerve. Information selected by the selecting device 510 and information on the shape of an optic nerve changed by the editing device 520 or information on the shape of an optic nerve newly produced by the editing device 520 is recorded by the recording unit 400.

The shape recording device 410 of the recording unit 400 reproduces, deletes, or copies information on the shape of an optic nerve specified by the selecting device 510 of the controller 500, updates information on the shape of an optic nerve changed by the editing device 520, and records additionally information on the shape of an optic nerve newly produced by the editing device 520. The shape recording device 410 is able to process information provided by an external editing unit 600. The external editing unit 600 is connected to the ophthalmological analyzer 1000 to edit information on the shape of an optic nerve. Therefore, information on the shape of an optic nerve can be processed for editing without interrupting the operation of the ophthalmological analyzer 1000. If system security is required, the shape recording device 410 is able to inhibit operations for processing information provided by the external editing unit 600. The test result recording device 420 of the recording unit is able to record information given thereto by the ophthalmic testing unit 100, information given thereto by the data input unit 200, the interim results and final results of analytical operations of the controller 500, information selected by the selecting device 510 of the controller 500, and information changed by the editing device 520 of the controller 500.

The controller 500 is capable of ophthalmic image data processing. The controller 500 is provided also with a distortion correcting device 530 and is able to correct the distortion of coordinates caused by measuring means when converting coordinates of positions into corresponding virtual coordinates.

Figure 2:
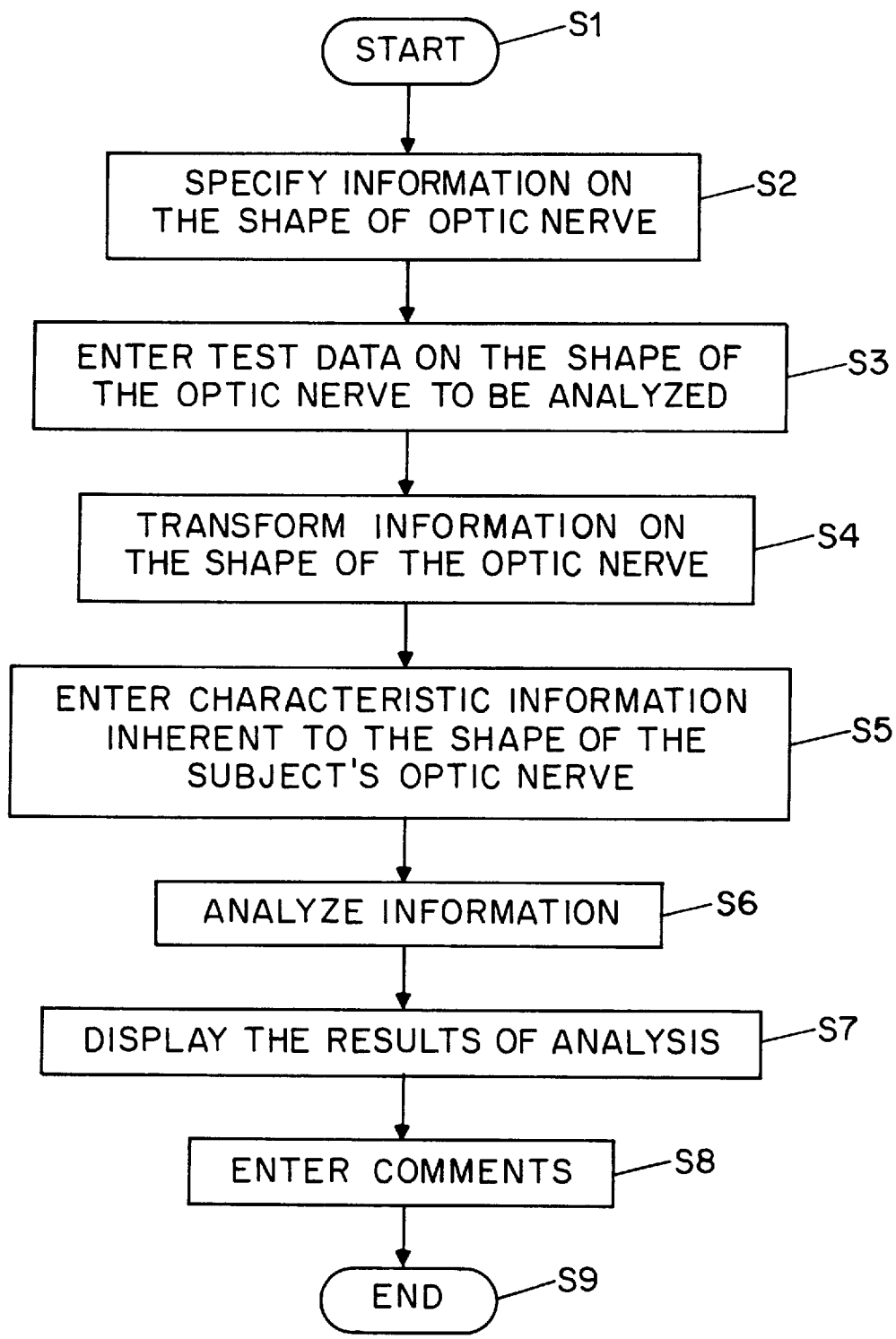
FIG. 2 is a flow chart of assistance in explaining the operation of the ophthalmological analyzer of FIG. 1.

The operation of the ophthalmological analyzer 1000 will be described with reference to FIG. 2. The ophthalmological analyzer 1000 starts its operation in step S1. In step S2 information on the shape of an optic nerve is specified. Information on the shape of an optic nerve is read from the shape recording device 410 by operating the data input unit 200 or information on the shape of an optic nerve produced by dictation is sent to the controller 500. If necessary, an operation for selecting the shape of an optic nerve may be repeated to obtain information on the shape of an appropriate optic nerve. In step S3, information on each test to be analyzed is inputted. Information on the test on subject is inputted from the ophthamological analyzer 1000, the inputted information is sent to the controller 500 and stored in the frame memory 311. Information effective for diagnosis including the subject's ID number, name, sex and age is retrieved from the test result recording device if the same is previously stored in the test result recording device 420 or the information is entered by operating the data input unit 200 if the same needs to be produced. The input information may be displayed for confirmation by the display 313 or may be recorded on the test result recording device 420. In step S4, the information on the shape of the optic nerve is subjected to conversion; that is, data representing the respective positions of the optic nerve papilla and the macula and the retinal boundary of the subject's eyeball is sent to the controller 500. the data representing the respective positions of the optic nerve papilla and the macula and the retinal boundary of the subject's eyeball is retrieved from or extracted automatically by image data processing from the test result recording device 420 or produced by operating the input unit 200. The position of the optic nerve papilla, the position of the macula and the retinal boundary can be offset by shifting the position of the optic nerve papilla, the position of the center of the macula and such by operating the data input unit 200.

Methods of converting the information on the shape of an optic nerve into information conforming to test data on the subject's visual field and eyeground will be described.

(1) A conversion method which enlarges, reduces or turns an image of an optic nerve on the basis of data representing the coordinates of the respective centers of the optic nerve papilla and the macula.

Figure 3:
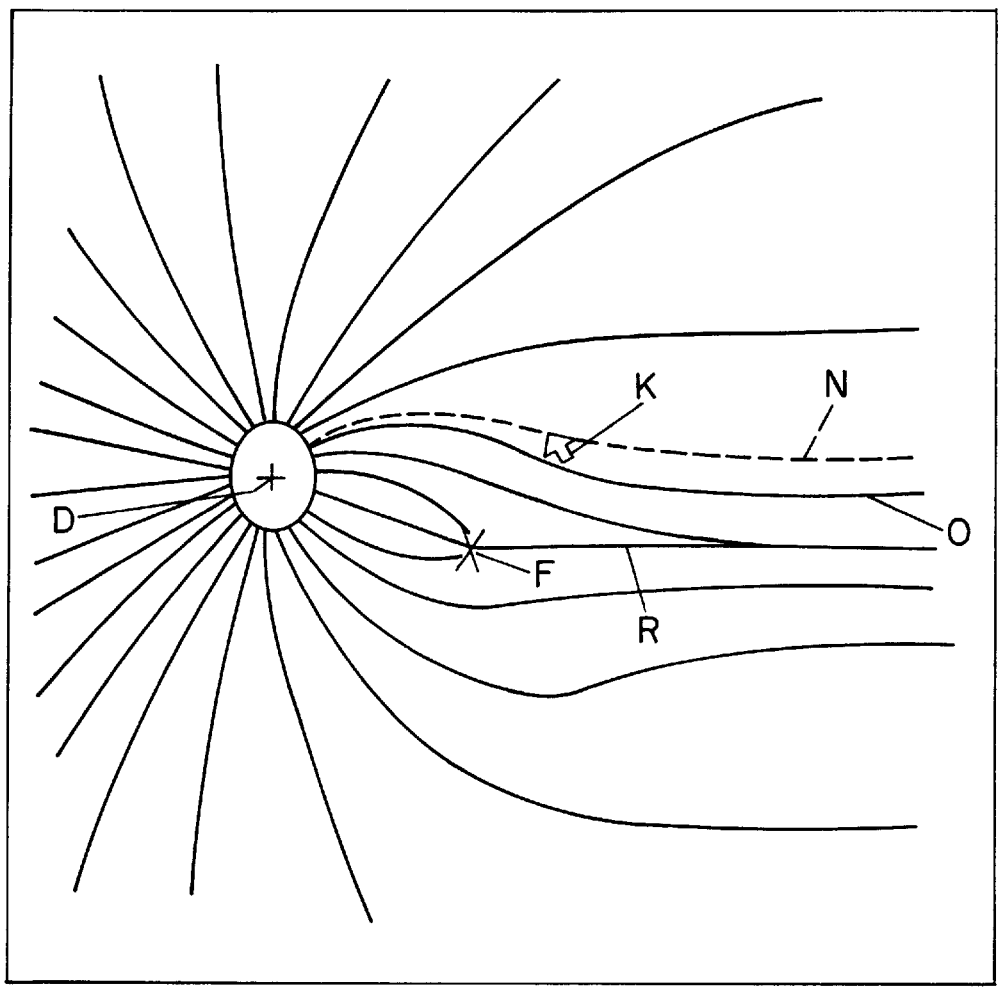
FIG. 3 is a diagrammatic view of an optic nerve.
Figure 4:
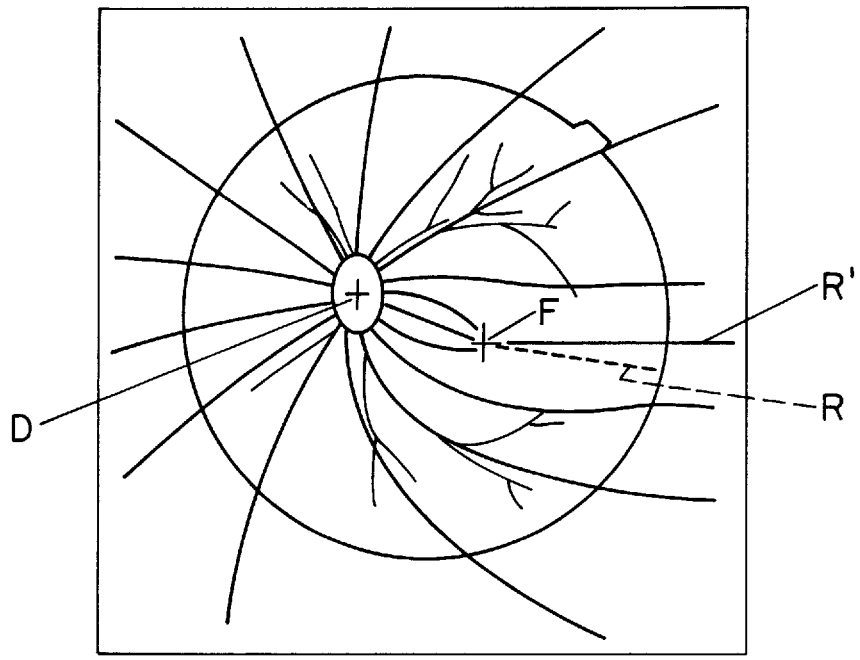
FIG. 4 is a diagrammatic view of assistance in explaining the conversion of information on an optic nerve to show the optic nerve in combination with the eyeground.

FIG. 3 shows an image of the optic nerve, in which D indicates the center of the optic nerve papilla, F indicates the center of the macula and R indicates the retinal boundary. FIG. 4 shows information on an optic nerve converted so as to conform to the eyeground, in which R' is the retinal boundary expressed by produced information on the shape of an optic nerve. This conversion method is able to make the center of the optic nerve papilla and the center of the macula represented by information on the eyeground coincide with those represented by information on the shape of the optic nerve. However, there is the possibility that the actual retinal boundary and a set retinal boundary do not coincide with each other.

(2) A conversion method which enlarges or reduces an image of an optic nerve on the basis of information on the distance between the respective centers of the optic nerve papilla and the macula, and turns the image so that the retinal boundary represented by the information on the shape of the optic nerve is horizontal.

Figure 5:
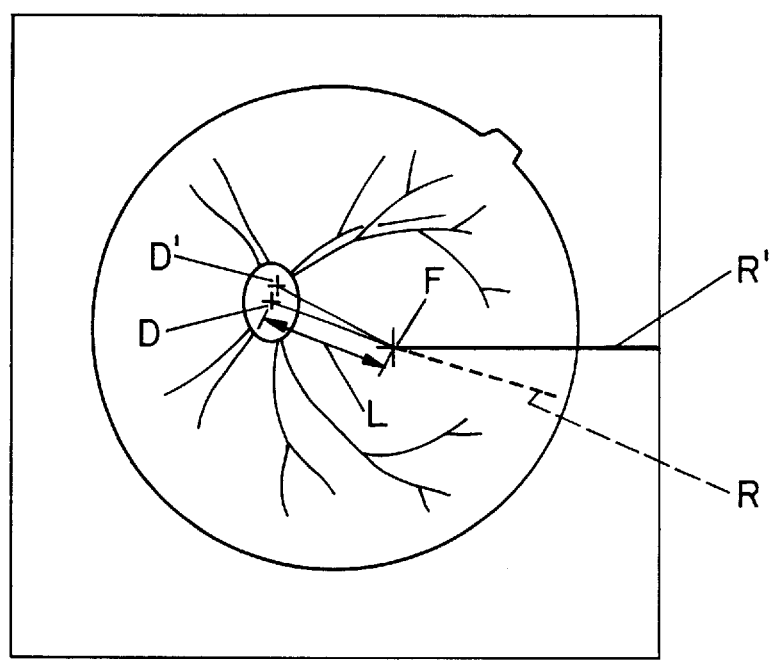
FIG. 5 is a diagrammatic view of assistance in explaining the conversion of information on an optic nerve to show the optic nerve in combination with the eyeground.

FIG. 5 shows an image of an optic nerve represented by information converted so that the image of the optic nerve conform to the eyeground, in which D' indicates the center of the optic nerve papilla represented by produced information on the shape of the optic nerve and R' indicates the retinal boundary represented by the produced information on the shape of the optic nerve. In FIG. 5, the indication of the shape of the optic nerve shown in FIG. 4 is omitted. Both the distance between D and F, i.e., the center D of the optic nerve papilla and the center F of the macula, and the distance between D' and F are L. When the information is transformed by this conversion method, the center of the macula represented by the set information on the shape of the optic nerve coincides with the actual eyeground. However, there is the possibility that the center of the optic nerve papilla and the retinal boundary do not coincide with each other. It is said the retinal boundary generally is horizontal.

(3) A conversion method which enlarges or reduces an image of an optic nerve on the basis of information on the distance between the respective centers of the optic nerve papilla and the macula, and turns the image so that the angle of the retinal boundary represented by the information on the shape of the optic nerve coincides with the angle of the subject's retinal boundary.

Figure 6:
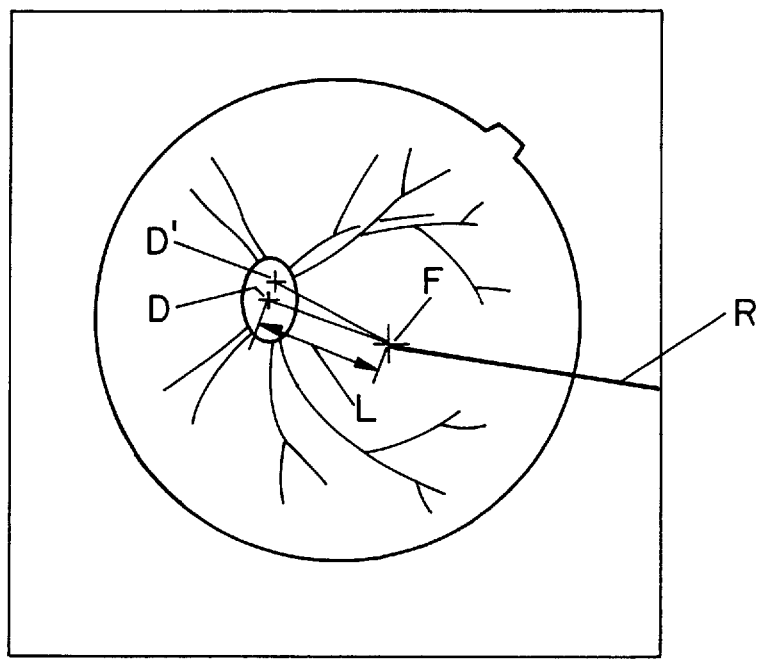
FIG. 6 is a diagrammatic view of assistance in explaining the conversion of information on an optic nerve to show the optic nerve in combination with the eyeground.

FIG. 6 shows an image of the optic nerve represented by information converted so as to conform to the eyeground. When converted by this conversion method, the actual eyeground coincides with the center of the macula and the retinal boundary represented by the set information on the shape of the optic nerve. However, there is the possibility that the actual eyeground does not coincide with the center of the optic nerve papilla. Parts shown in FIG. 6 and indicated by the same characters as those used in FIG. 5 are the same as those shown in FIG. 5 and hence the description thereof will be omitted.

(4) A conversion method which enlarges, reduces or turns an image of the optic nerve on the basis of information on the respective centers of the optic nerve papilla and the macula, and the angle of the retinal boundary.

Figure 7:
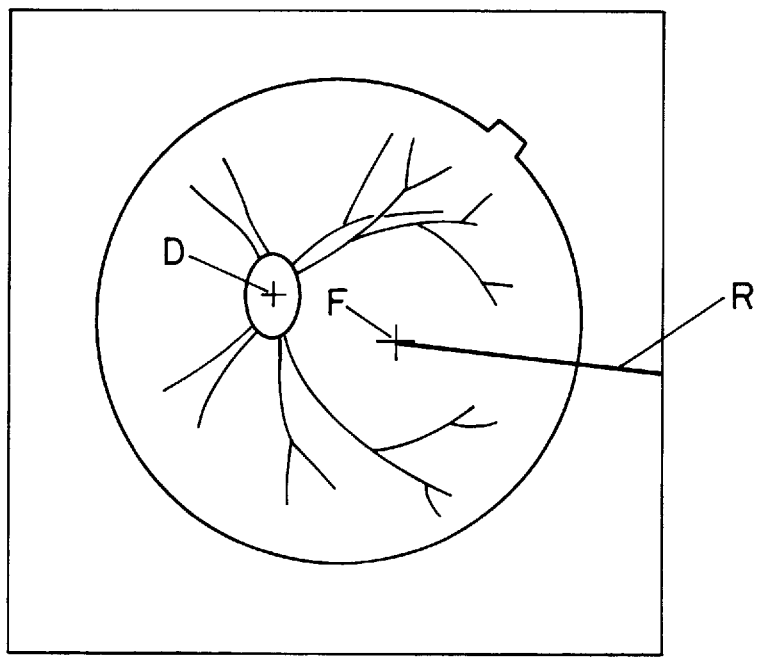
FIG. 7 is a diagrammatic view of assistance in explaining the conversion of information on an optic nerve to show the optic nerve in combination with the eyeground.

FIG. 7 shows an image represented by information on the optic nerve transformed so as to conform to the eyeground. When converted by this conversion method, the actual eyeground coincides with the respective centers of the optic nerve papilla and the macula and the retinal boundary represented by set information on the shape of the optic nerve. However, the conversion method takes time and labor. Parts shown in FIG. 7 and indicated by the same characters as those used in FIGS. 5 and 6 are the same as those shown in FIGS. 5 and 6 and hence the description thereof will be omitted.

A desired one of the conversion methods (1) to (4) may be selected by operating the data input unit 200, the previously used conversion method may be called from the recording unit 400 or a predetermined standard conversion method may be specified.

The converted shape of the optic nerve can be displayed on the screen of the display 313 or the converted shape of the optic nerve can be displayed in combination with test results provided by the ophthalmic testing unit 100 on the screen of the display 313 for the examination of the data or for the examination of processes to try the test over again. The conversion method used in step S4 may be recorded on the test result recording device 420.

In step S5, characteristic information inherent to the shape of the subject's optic nerve is entered. If the shape of the optic nerve converted in step S4 does not conform exactly to the test results obtained by testing the subject's eyeball due to the subject's individual difference and differences in test conditions, the converted shape of the optic nerve is changed so as to conform to the test results by a method, which will be explained later. The information inherent to the subject and the test results may be recorded on the test result recording device 420.

An analytical operation is carried out in step S6. The controller 500 transforms the coordinates of positions received from the ophthalmic testing unit 100 into corresponding virtual coordinates, and calculates the correspondence between the virtual coordinates and positions on the optic nerve (the direction of the optic nerve and the distance between the optic nerve and the optic nerve papilla) to determine the positions of the test results provided by the ophthalmic testing unit 100 on the optic nerve.

When transforming the coordinates of the positions provided by the ophthalmic testing unit 100 into the virtual coordinates, the distortion of the coordinates due to the measuring means may be corrected by the distortion correcting device 530. For example, a retinal photograph taken by the retinal tester 110 shows the construction of the eyeball in a two-dimensional picture. Therefore, the photograph has a fundamental distortion in addition to a distortion inherent to the retinal tester 110. Since the coordinates of measured points are expressed by angles of visibility, the data on the visual field provided by the perimeter 120 is distorted if the data on the visual field is transferred directly to the virtual coordinates on a plane.

If the virtual coordinates are plotted in a space defined by a three-dimensional coordinate system in view of the shape of the eyeball, the influence of the distortion of the position coordinates on the photograph of the eyeground can be reduced.

Suppose that the virtual coordinates are represented by an angle θ of deviation from a center line, and a direction (phi) of deviation. Then, the virtual coordinates can simply be determined by using a plane including the center of the lens and perpendicular to the optical axis of the lens as a major plane. The angle θ of deviation is an angle to the optical axis, the direction of deviation (phi) is an angle of deviation to the optical axis. Since the eyeball can be regarded as a sphere, the three-dimensional spherical space can be defined only by the angle and the direction of deviation (phi). As regards the direction of deviation (phi), there is no theoretical error between the eyeground and the visual field. The angle θ of deviation includes an error produced when projecting the spherical shape on a plane.

Figure 8:
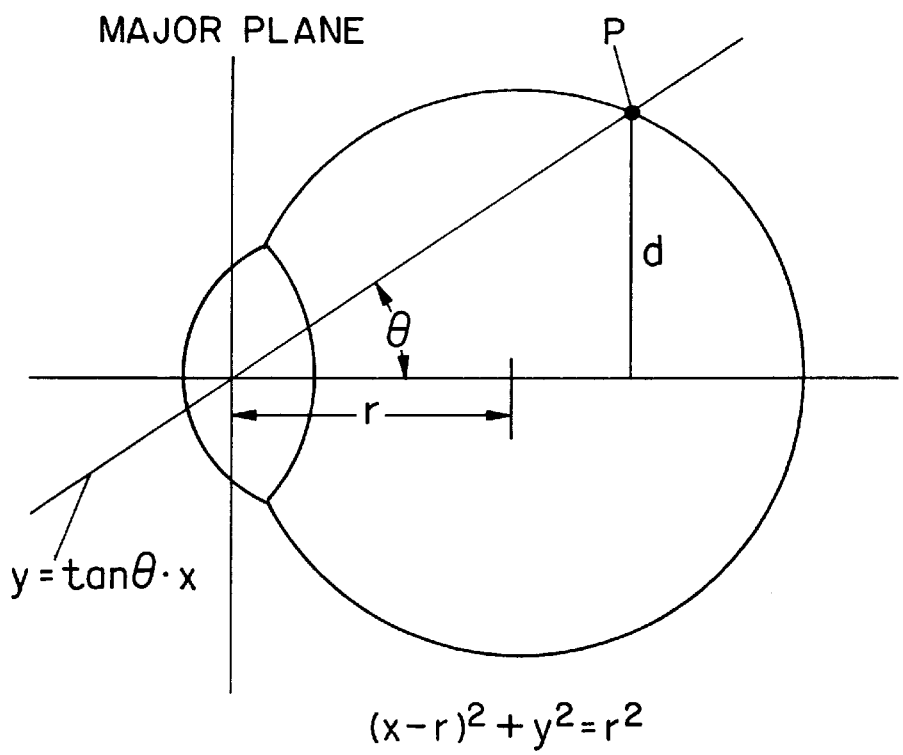
FIG. 8 is a sectional view of an eyeball with respect to an optional direction of deviation (phi)
Figure 9:
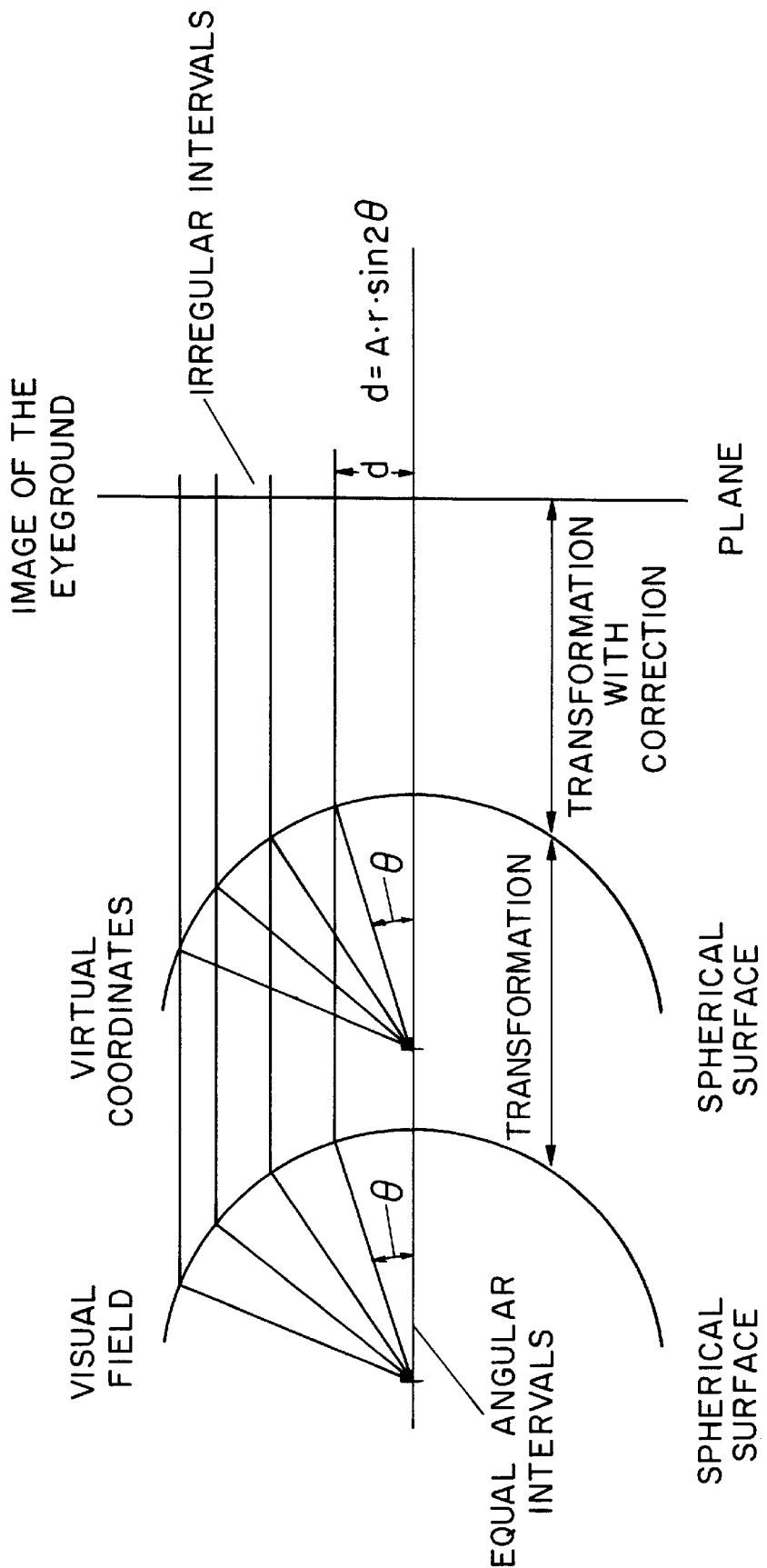
FIG. 9 is diagram of assistance in explaining errors when a visual field and an eyeground are superposed.
Figure 10:
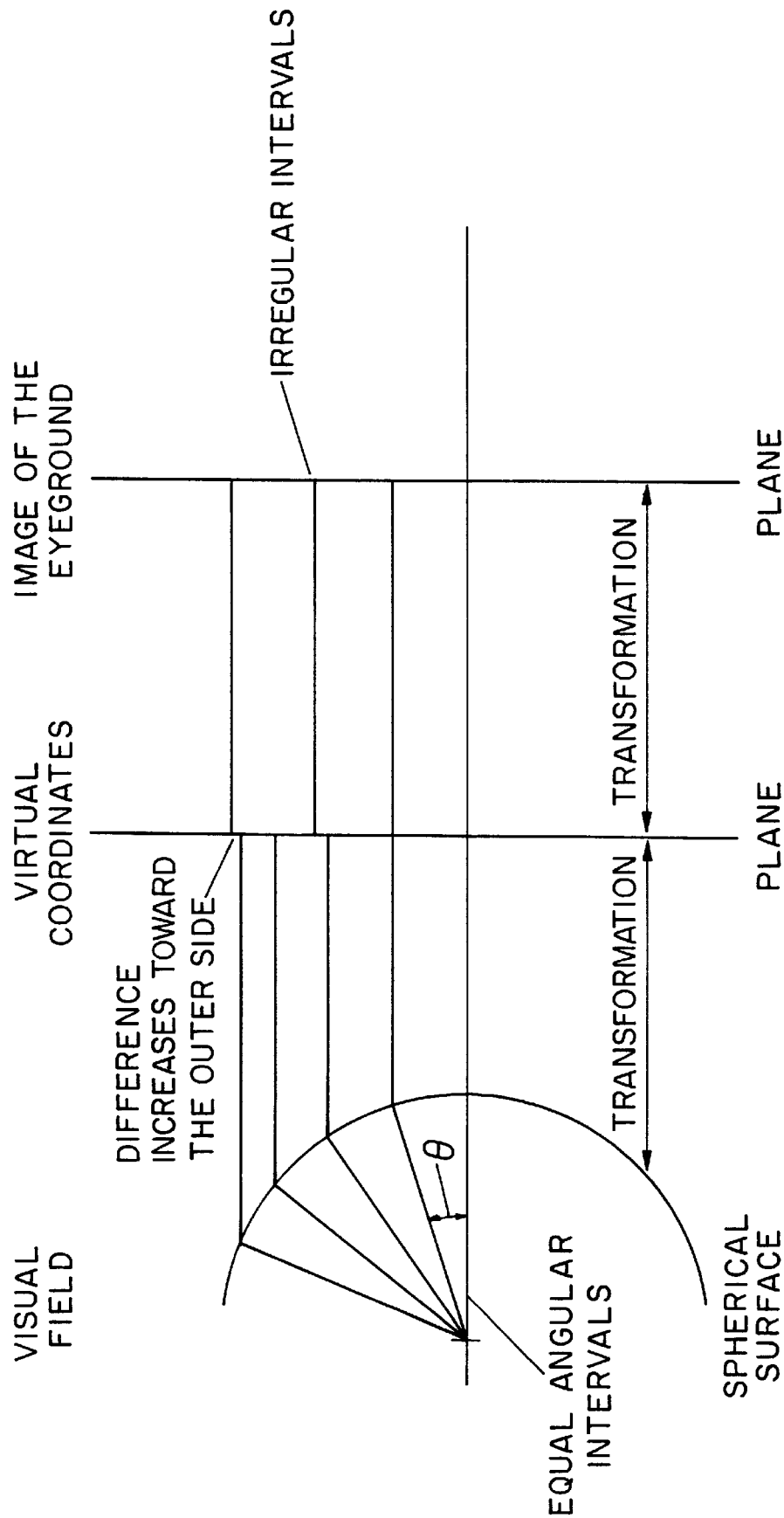
FIG. 10 is a diagram of assistance in explaining the use of actual dimensions for virtual coordinates without the precision correction of distortion.
Figure 11:
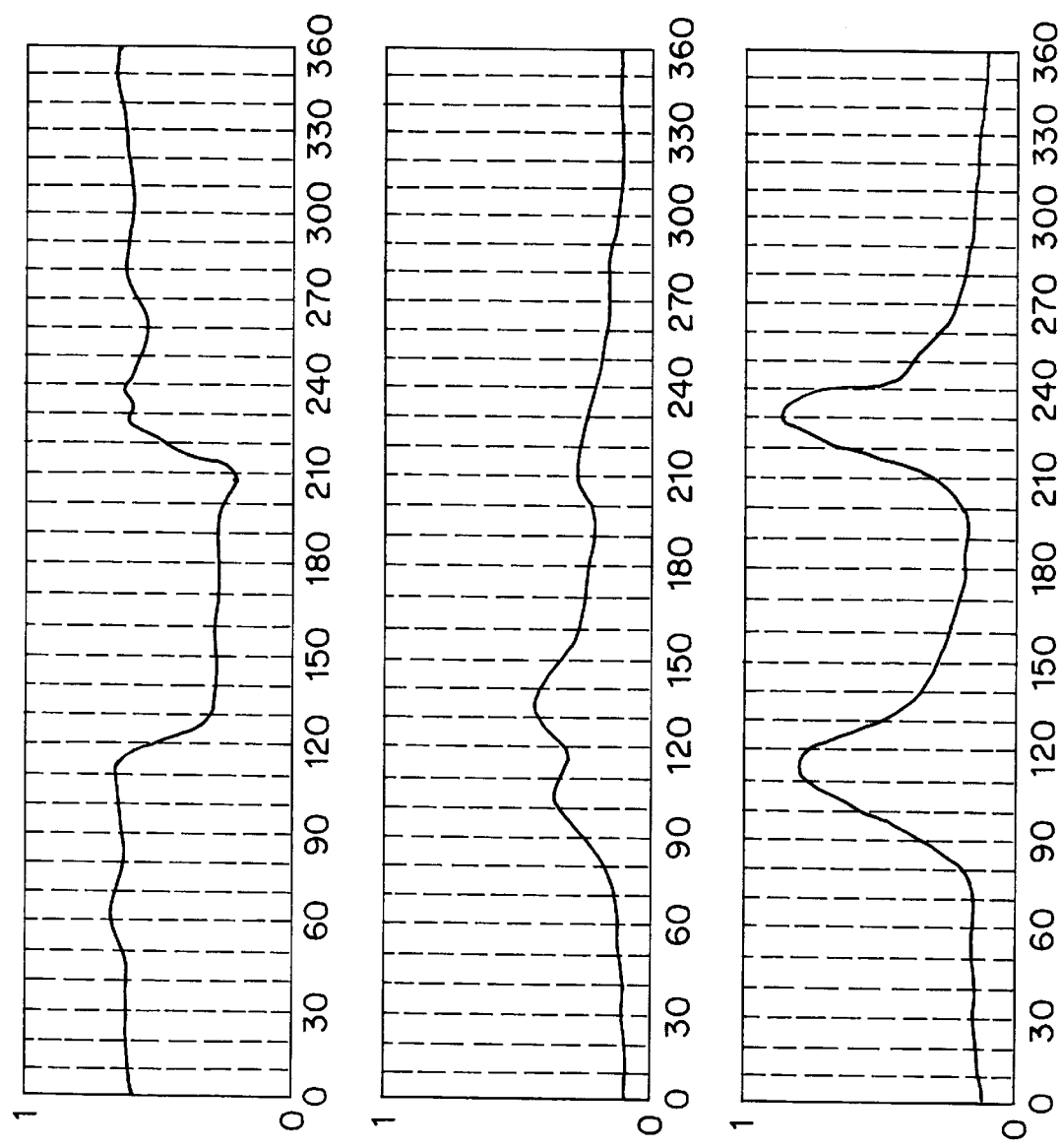
FIG. 11 is a pictorial view showing a picture displayed on the screen of a display.
Figure 12:
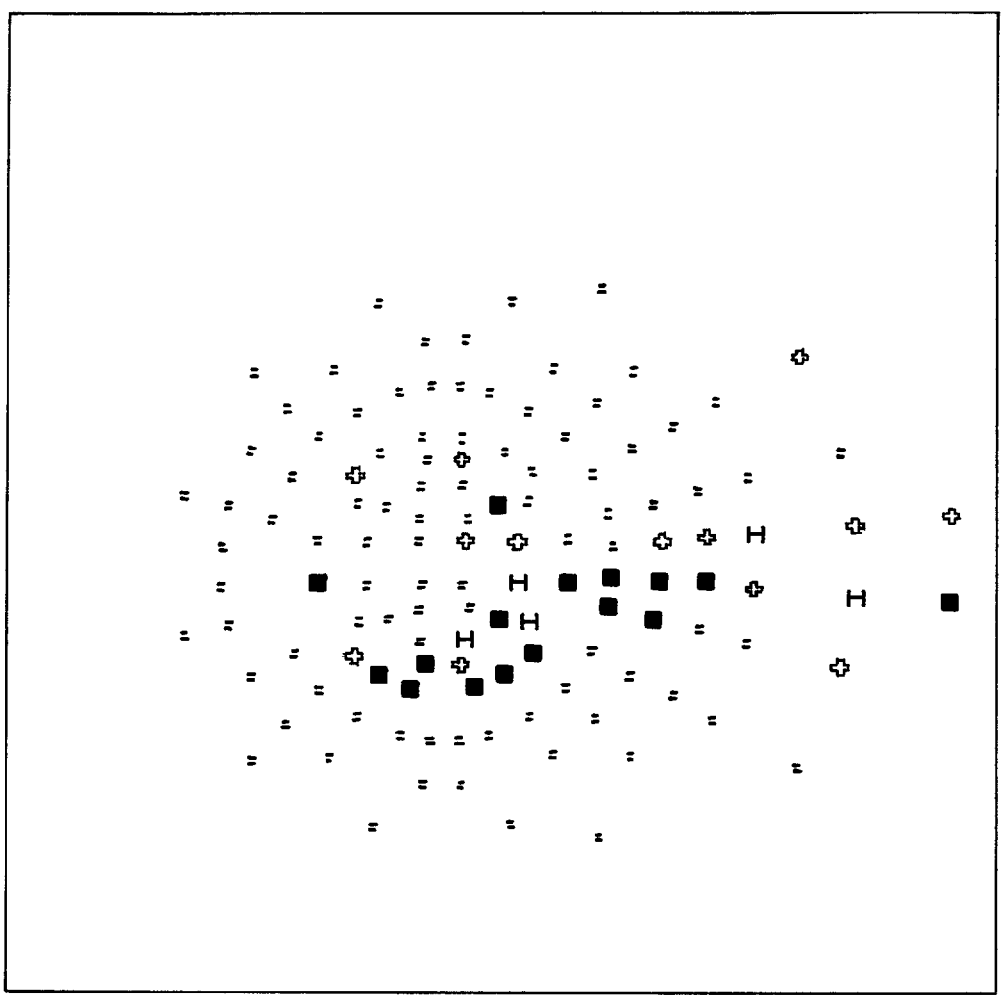
FIG. 12 is a pictorial view showing a picture displayed on the screen of a display.
Figure 13:
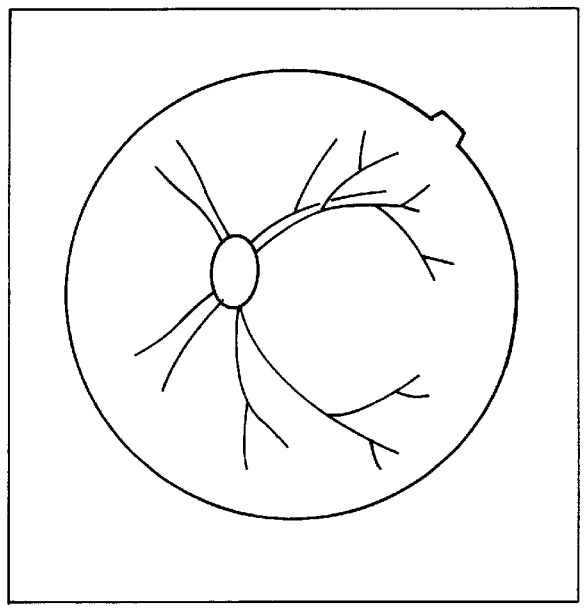
FIG. 13 is a pictorial view showing a picture displayed on the screen of a display.
Figure 14:
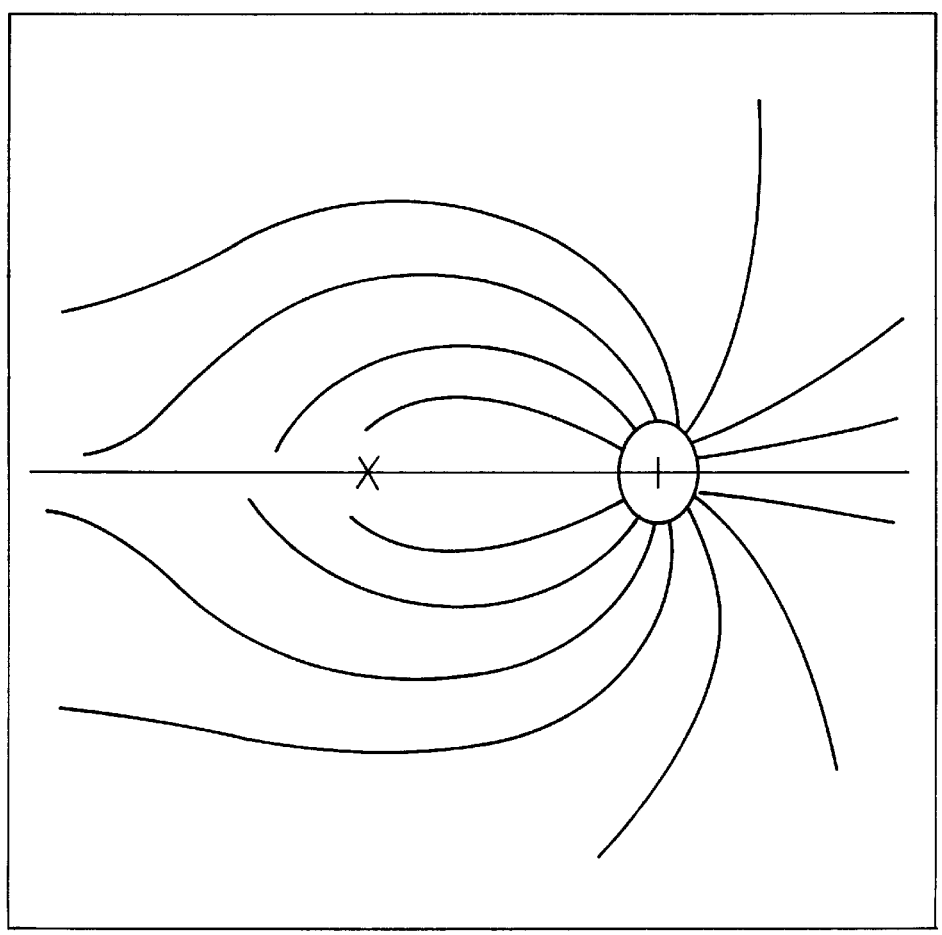
FIG. 14 is a pictorial view showing a picture displayed on the screen of a display.
Figure 15:
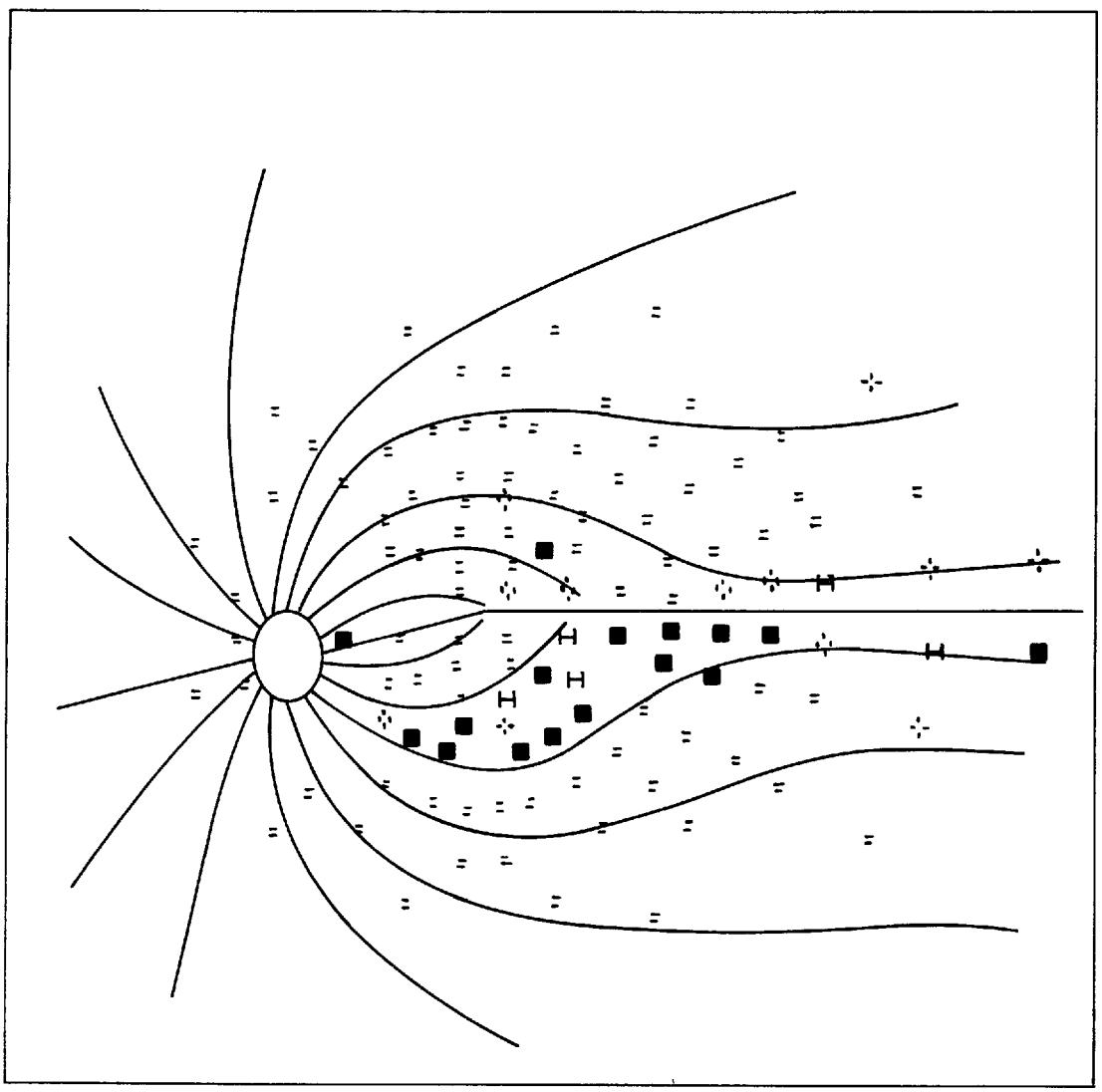
FIG. 15 is a pictorial view showing a picture displayed on the screen of a display.
Figure 16:
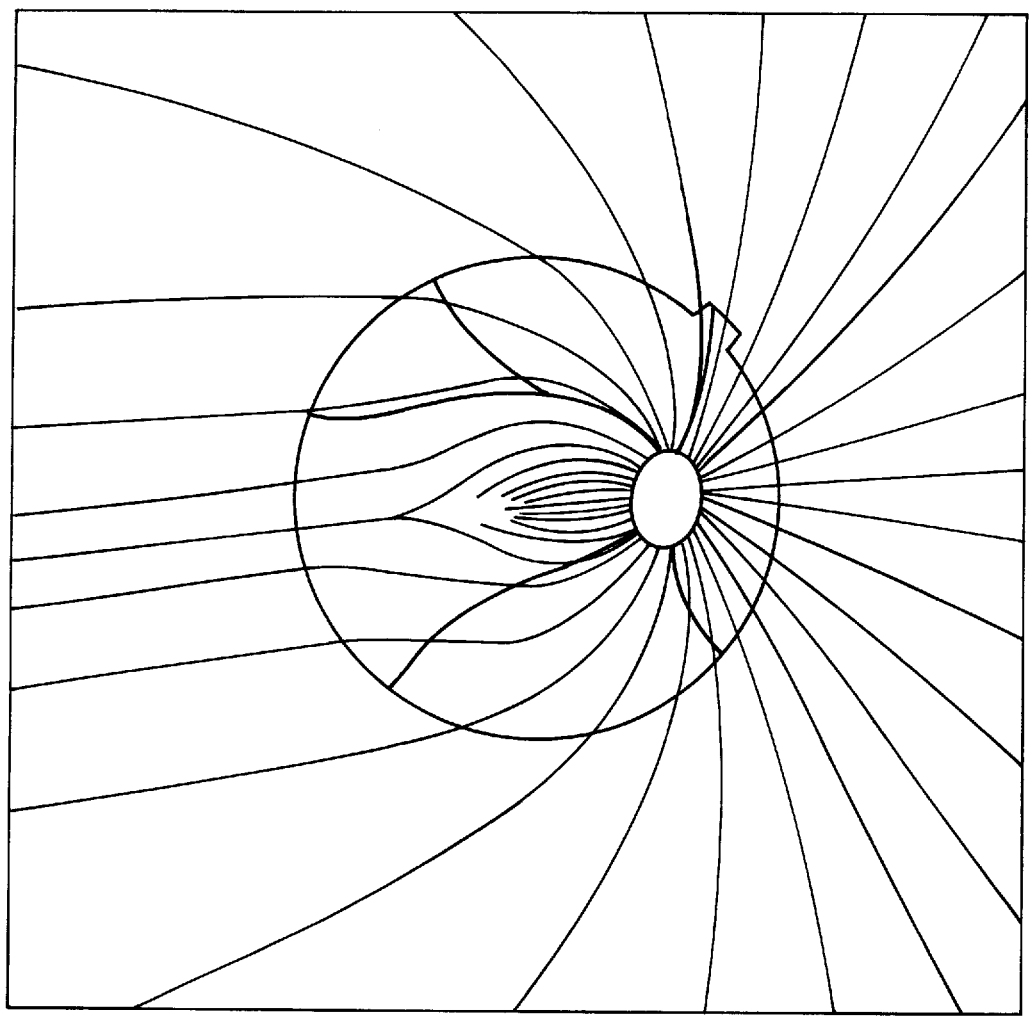
FIG. 16 is a pictorial view showing a picture displayed on the screen of a display.
Figure 17:
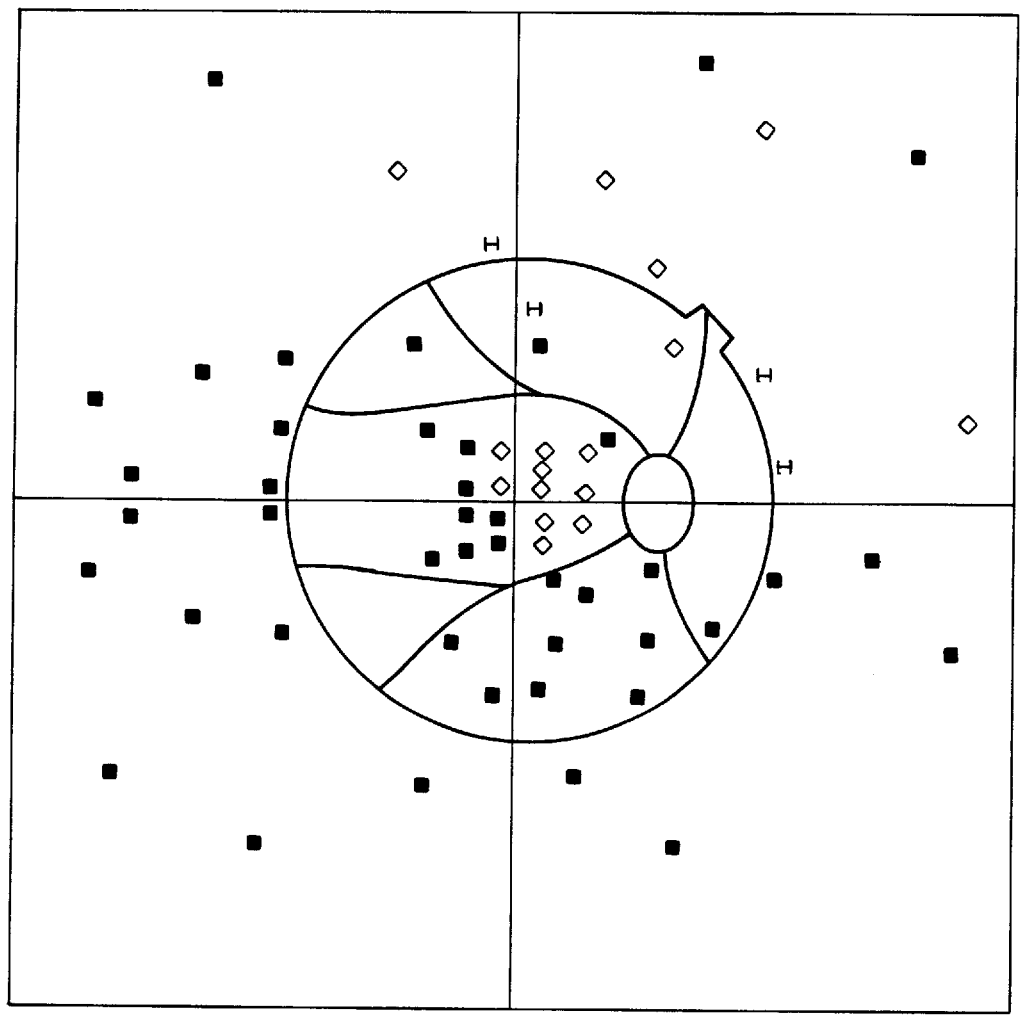
FIG. 17 is a pictorial view showing a picture displayed on the screen of a display.
Figure 18:
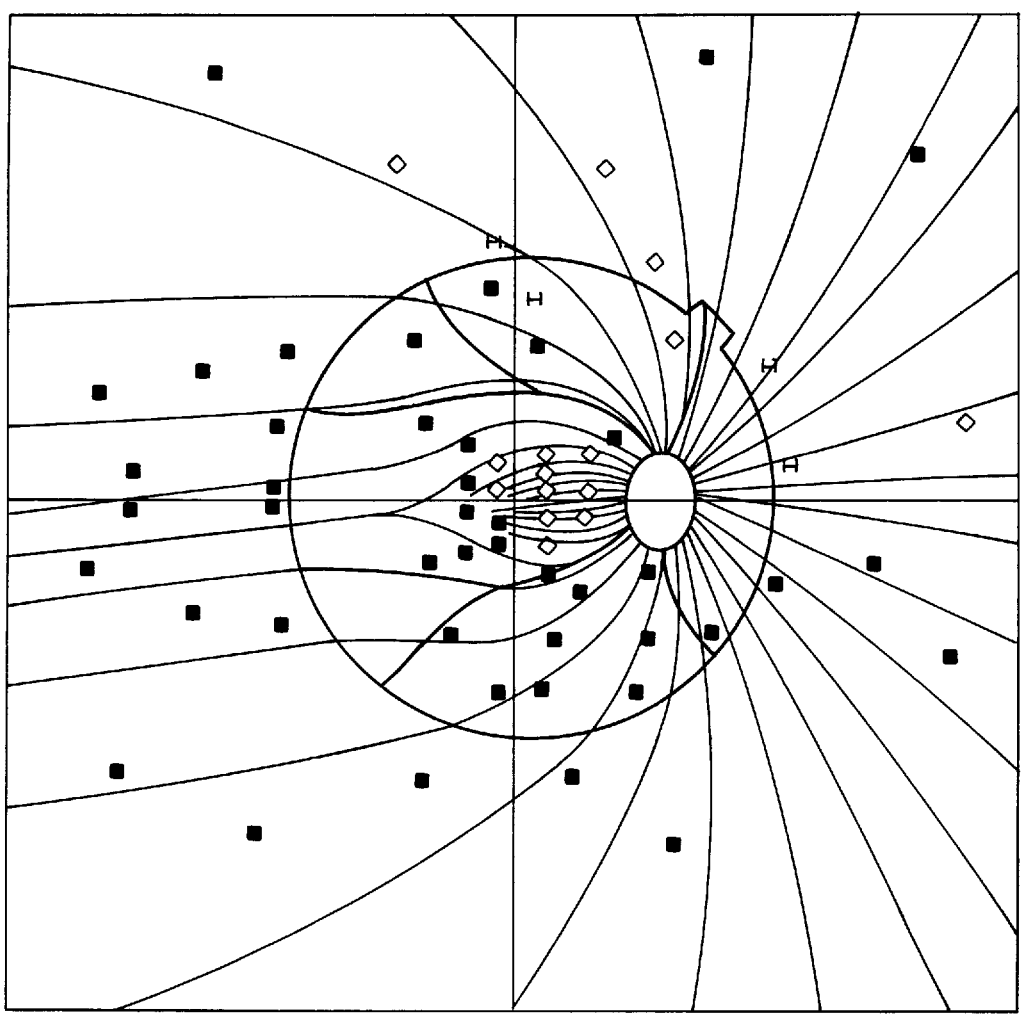
FIG. 18 is a pictorial view showing a picture displayed on the screen of a display.

FIG. 8 is a sectional view of an eyeball with respect to an optional direction of deviation (phi). A position on the eyeground is expressed by:

$$d = A \cdot r \sin 2\theta$$

where d is the distance between the position and the optical axis, θ is the angle of deviation, r is equal to half the length of the axis of the eyeball, A is the ratio of an image on the eyeground to the length 2r of the axis of the eyeball. The length of the axis of the eyeball may be the mean of measured lengths of the axes of eyeballs or an actual measured length of the axis of the eyeball. Accordingly, as shown in FIG. 9, the coordinates of positions on the eyeground further from the optical axis are distorted more greatly, and the simple superposition of the visual field and the eyeground produces errors. Therefore, if the angle θ is expressed by:

$$\theta = (\tfrac{1}{2}) \cdot \sin^{-1} (d/(A \cdot r))$$

the visual field and the eyeground can accurately be superposed by transforming the coordinates into the corresponding virtual coordinates.

In an ordinary state of use, the foregoing precision correction is not carried out and actual dimensions are used for virtual coordinates without the precision correction of distortion to simplify the process because the image of the eyeground is not separated by a great distance from the optical axis in an ordinary state of use.

Since this embodiment is able to indicate the positions tested by the ophthalmic testing unit 100 by the same coordinates, the integral analysis of the distribution of the visual field on the optic nerve fibers, the distribution of lesions on the eyeground, and the overlap of the visual field and lesions on the eyeground is possible. Graphs and tables showing the results of analysis can be displayed on the screen of the display 313 and can be printed out by the printer 320.

In step S7, the results of analysis is provided. The display 313 is able to display the test results provided by the ophthalmic testing unit 100, a modified shape of the optic nerve, and data obtained by combining the test results provided by the ophthalmic testing unit 100 and the shape of the optic nerve read from the test results recording device 420 in addition to the results of analysis. Thus, the object of analysis and the results of analysis can simultaneously be examined.

FIGS. 11 to 18 show pictures displayed on the screen of the display 313. If the results of analysis of the same disease obtained at different times are recorded, the variation of the disease with time can be examined by simultaneously displaying those results of analysis on the screen of the display 313. If a clinically useful picture can be displayed, the data representing the picture may be recorded on the test result recording device 420 or may be printed out by the printer 320.

In step S8, comments are entered. The test results and the results of analysis are examined, a diagnosis and comments may be displayed in combination with the foregoing useful picture on the screen of the display 313, and may be recorded on the test result recording device 420. Thus the ophthalmological analyzer 1000 is able to serve as an image file and an electronic clinical recorder.

In step S9, the operation of the ophthalmological analyzer 1000 is ended and, if necessary, step S1 and the following steps can be repeated.

Figure 19:
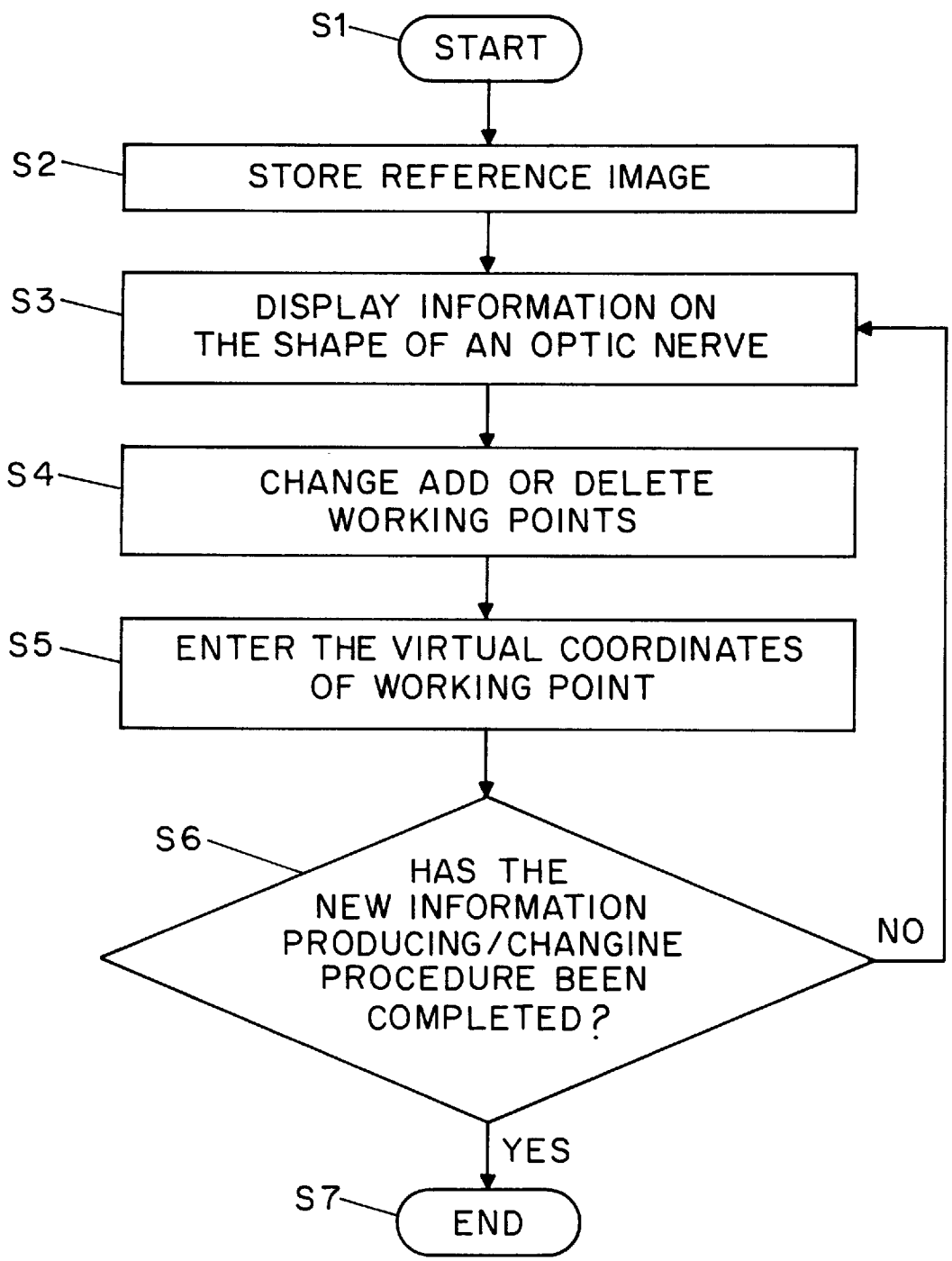
FIG. 19 is a flow chart of assistance in explaining the operation of the ophthalmological analyzer embodying the present invention.

The production/change of new information on the shape of an optic nerve to be carried out in steps S2 and S5 will be described with reference to FIG. 19. It is assumed, to simplify the description, that the actual dimensions of the optic nerve are indicated by virtual coordinates and information on the shape of the optic nerve is available from a look-up table.

In step S1, a new information producing/changing procedure for producing/changing new information on the shape of an optic nerve is started. If the change of information on the shape of the optic nerve is required, a look-up table carrying information on the shape of the optic nerve to be changed is read from the shape recording device 410. If the production of new information on the shape of the optic nerve is required and basic information on the shape of the optic nerve is available, a look-up table carrying the basic information on the shape of the optic nerve is read from the shape recording device 410.

In step S2, a reference image is stored. If coordinates of the eyeground and data representing images of the optic nerve fibers and such are available, the coordinates and the data are entered to store on the frame memory 311. If a photograph of the eyeground is used as a reference, a look-up table precisely representing the shape of the optic nerve fibers inherent to the photograph of the eyeground is produced. Only data representing portions around the optic nerve papilla and the macula can be used as reference data. A model of optic nerve fibers may be the Hogan's model or the Harrington's model. An appropriate model of optic nerve fibers is selected, taking into consideration the object of analysis and such. Although the Hogan's model is very precise, the shape of the retinal boundary is inappropriate. However, the inappropriate shape of the retinal boundary comes into question only with an outer visual field and hence the Hogan's model is effective in use in a relatively narrow range. Although the Harrington's model is simpler than the Hogan's model, the shape of the retinal boundary in the Harrington's model is appropriate, and hence the Harrington's model is effective in use in a relatively wide range.

In step S3, information on the shape of the optic nerve is displayed. Virtual coordinates and coordinates indicating positions on the optic nerve are shown in pairs in the look-up table. A necessary number of pairs are shown. If actual dimensions are used for the virtual coordinates, coordinates of the actual dimensions with respect to an origin at an appropriate position, and coordinates indicating positions on the optic nerve (the direction of the optic nerve, and the distance from the optic nerve papilla) are recorded in the following forms.

| Look-up Table in Example 1 | | | | |
|---|---|---|---|---|
| X-coordinate of actual dimension | ... | ... | ... | ... |
| Y-coordinate of actual dimension | ... | ... | ... | ... |
| Direction of optic nerve (angle) | ... | ... | ... | ... |
| Distance from optic nerve papilla | | ... | ... | ... |

The direction (angle) of the optic nerve is optic nerve angle when the center of the optic nerve papilla is at the origin and the direction of the macula is 180°. The distance from the optic nerve papilla is the distance from the center of the optic nerve papilla relative to the distance between the optic nerve papilla and the macula. A magnification necessary when superposing the distance between the optic nerve papilla and the macula indicated by coordinates of actual dimensions in the look-up table, and the distance between the optic nerve papilla and the macula in the foregoing reference image can be determined on the basis of the ratio between the distance between the optic nerve papilla and the macula indicated by coordinates of actual dimensions in the look-up table, and the distance between the optic nerve papilla and the macula in the foregoing reference image. When coordinates of actual dimensions in the look-up table are subjected to affine transformation so that the coordinates of the optic nerve papilla and the macula in the look-up table coincide with the coordinates of the optic nerve papilla and the macula in the reference image, and the adjacent pints are interconnected, the shape of the optic nerve described in the look-up table can be expressed. The information on the shape of the optic nerve obtained from the look-up table is stored in the overlay memory 312, the respective contents of the frame memory 311 and the overlay memory 312 are combined, and information produced by combining the respective contents of the frame memory 311 and the overlay memory 312 may be displayed on the screen of the display 313.

Although the foregoing embodiment uses actual dimensions for the virtual coordinates, coordinates determined taking into consideration the shape of the eyeball may be used if further precision analysis is necessary. For example, when the origin of the virtual coordinate system is the fixation point of the visual field (or the position of the macula on the eyeground) and the fixation point is expressed by the direction of deviation (phi) from the origin and the angle θ of deviation, a virtual coordinates determined by taking into consideration the shape of the eyeball can be obtained. A Look-up table in Example 2 developed by taking the shape of the eyeball into consideration is shown below.

| Look-up Table in Example 2 | | | | |
| --- | --- | --- | --- | --- |
| Direction of deviation (phi) | ... | ... | ... | ... |
| Angle θ of deviation | ... | ... | ... | ... |
| Direction of optic nerve (angle) | ... | ... | ... | ... |
| Distance from optic nerve papilla | ... | ... | ... | ... |

The look-up table in Example 1 has a tendency to provide virtual coordinates flatter than eyeground coordinates, and the look-up table in Example 2 has a tendency to provide virtual coordinates more spherical than visual field coordinates. In either the look-up table in Example 1 or the look-up table in Example 2, it is possible to make the coordinates of the visual field and those of the eyeground identical by transforming the coordinates of the visual field into virtual coordinates and transforming the coordinates of the eyeground into virtual coordinates.

In step S4, operations for changing working points, adding working points and deleting working points are carried out, observing a picture displayed on the screen of the display 313. The working point is indicated by a set of coordinates, i.e., X-coordinate of actual dimension, Y-coordinate of actual dimension, direction (angle) of the optic nerve, and distance from the optic nerve papilla. In this embodiment, coordinates of actual dimensions indicating the working point are entered.

Figure 20:
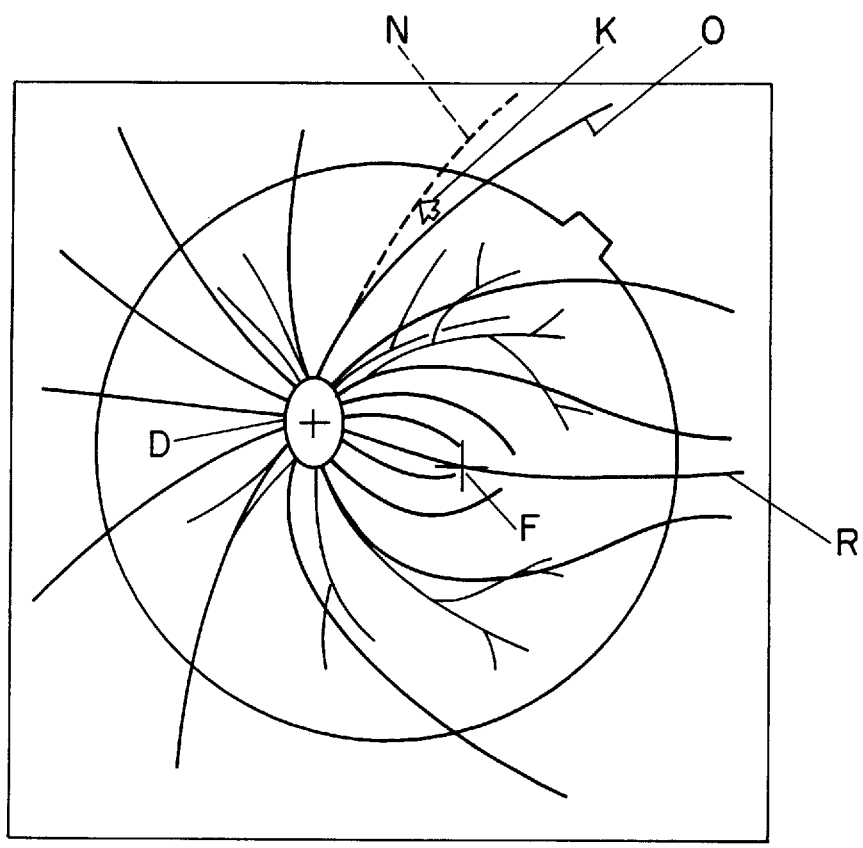
FIG. 20 is a pictorial view of assistance in explaining a method of changing a working point.

FIGS. 3 and 20 are views of assistance in explaining a method of changing a working point. FIG. 3 does not include any reference image, and FIG. 20 includes an image of the eyeground as a reference image. A working point can be selected by moving a cursor K by the mouse 220. In FIGS. 3 and 20, information O on the shape of the optic nerve to be changed is selected by moving the cursor to a position on the information O, and the information O is moved to new coordinates N.

In step S5, virtual coordinates of the working point is entered. The position of the specified working point on the optic nerve is entered, observing an image displayed n the screen of the display 313. In the look-up table in Example 1, the position on the optic nerve is expressed by the direction (angle) of the optic nerve and the distance from the optic nerve papilla. In this embodiment, the data input unit 200 is operated to enter data on the direction (angle) of the optic nerve and the distance from the optic nerve papilla.

In step S6, a query is made to see if the new information producing/changing procedure has been completed. The operation returns to step S3 if the response in step S6 is negative, or the new information producing/changing procedure is ended if the response in step S6 is affirmative. Information on the shape of the optic nerve, thus produced is recorded on the shape recording device 410.

In the ophthalmological analyzer of the present invention, the recording unit records at least the test data on subjects and the information on the shape of the optic nerve, the data input unit is operated by a tester to enter characters and values of coordinates, and the controller analyzes test data on the subjects, and information on the shape of the optic nerve, read from the recording unit. The controller is capable of selecting a piece of information to be used from a plurality of pieces of information on the shapes of a plurality of optic nerves, of changing at least part of information on the shape of an optional optic nerve or of producing information on the shape of a new optic nerve. Accordingly, the ophthalmological analyzer is flexible in operation, for example, to change the shape of the optic nerve.

What is claimed is:

1. An ophthalmological analyzer comprising:
   a recording unit for recording at least test data on subjects and information on shapes of optic nerves;
   a data input unit to be operated by a tester to enter characters and values for coordinates; and
   a controller which carries out an analytical operation on the basis of the test data on the subject and the information on the shape of an optic nerve, read from the recording unit;
   wherein the controller is capable of selecting a piece of information to be used from a plurality of pieces of information on the shapes of a plurality of optic nerves, of changing at least part of information on the shape of an optional optic nerve or of producing information on the shape of a new optic nerve.

2. The ophthalmological analyzer according to claim 1, wherein the controller is provided with a selecting means for selecting the information on the shape of an optional optic nerve among a plurality of pieces of information on the shapes of optic nerves recorded on the recording unit.

3. The ophthalmological analyzer according to claim 1, wherein the controller is provided with an editing means for changing the information on the shapes of optic nerves, recorded on the recording unit or producing new information on the shapes of optic nerves.

4. The ophthalmological analyzer according to claim 1, wherein the controller is capable of enlarging, reducing or turning the information on the shape of an optic nerve read from the recording unit on the basis of input data entered by operating the data input unit or information on the coordinates of the center of an optic nerve papilla and the center of a macula, read from the recording unit to make the information on the shape of an optic nerve read from the recording unit conform to the test results of an eyeground or a visual field to be analyzed.

5. The ophthalmological analyzer according to claim 1, wherein the controller is capable of enlarging, reducing or turning the information on the shape of an optic nerve read from the recording unit on the basis of input data entered by operating the data input unit or information on the distance between the center of an optic nerve papilla and the center of a macula, read from the recording unit to make the information on the shape of an optic nerve read from the recording unit conform to the test results of an eyeground or a visual field to be analyzed.

6. The ophthalmological analyzer according to claim 1, wherein the controller is capable of enlarging, reducing or turning the information on the shape of an optic nerve read from the recording unit on the basis of input data entered by operating the data input unit or information on the distance between the center of an optic nerve papilla and the center of a macula, read from the recording unit and of turning the angle of a retinal boundary specified by the information on the shape of an optic nerve so as to coincide with the angle of the subject's retinal boundary to make the information on the shape of an optic nerve read from the recording unit conform to the test results of an eyeground or a visual field to be analyzed.

7. The ophthalmological analyzer according to claim 1, wherein the controller is capable of enlarging, reducing or turning the information on the shape of an optic nerve read from the recording unit on the basis of input data entered by operating the data input unit or information on the center of an optic nerve papilla, the center of a macula, and the angle of retinal boundary included in information on the shape of an optic nerve read from the recording unit to make the information on the shape of an optic nerve read from the recording unit conform to the test results of an eyeground or a visual field to be analyzed.

8. The ophthalmological analyzer according to claim 1, wherein controller is capable of enlarging, reducing or turning the information on the shape of an optic nerve read from the recording unit on the basis of input data entered by operating the data input unit to make the information on the shape of an optic nerve read from the recording unit conform to the test results of an eyeground or a visual field to be analyzed.

9. The ophthalmological analyzer according to claim 1, wherein the controller is provided with a distortion correcting means for obtaining corrected information on the shape of an optic nerve produced by correcting the distortion of the information on the shape of an optic nerve, and is capable of transforming the coordinates of the ophthalmic testing unit without entailing distortion.

* * * * *